(12) United States Patent
Prudnikov et al.

(10) Patent No.: US 7,666,202 B2
(45) Date of Patent: Feb. 23, 2010

(54) ORBITAL ATHERECTOMY DEVICE GUIDE WIRE DESIGN

(75) Inventors: Dmitriy Prudnikov, New Hope, MN (US); Svenn Edvin Borgersen, Eagan, MN (US)

(73) Assignee: Cardiovascular Systems, Inc., St. Paul, MN (US)

(*) Notice: Subject to any disclaimer, the term of this patent is extended or adjusted under 35 U.S.C. 154(b) by 901 days.

(21) Appl. No.: 10/793,980

(22) Filed: Mar. 5, 2004

(65) Prior Publication Data
US 2005/0209615 A1   Sep. 22, 2005
US 2006/0142793 A9   Jun. 29, 2006

Related U.S. Application Data

(63) Continuation-in-part of application No. 10/753,040, filed on Jan. 7, 2004, now abandoned.

(51) Int. Cl.
  *A61B 17/14*   (2006.01)
  *A61B 17/32*   (2006.01)
(52) U.S. Cl. .................................. 606/180; 606/170
(58) Field of Classification Search ................. 606/108
   See application file for complete search history.

(56) References Cited

U.S. PATENT DOCUMENTS

| | | | |
|---|---|---|---|
| 4,990,134 A | 2/1991 | Auth | |
| 5,217,474 A | 6/1993 | Zacca et al. | |
| 5,312,427 A | 5/1994 | Shturman | |
| 5,314,438 A | 5/1994 | Shturman | |
| 5,700,243 A | 12/1997 | Narciso, Jr. | |
| 5,897,566 A | 4/1999 | Shturman et al. | |
| 6,132,444 A | 10/2000 | Shturman et al. | |
| 6,371,971 B1 * | 4/2002 | Tsugita et al. | 606/200 |
| 6,468,291 B2 * | 10/2002 | Bates et al. | 606/200 |
| 6,494,890 B1 | 12/2002 | Shturman et al. | |
| 6,893,451 B2 * | 5/2005 | Cano et al. | 606/200 |
| 7,118,539 B2 * | 10/2006 | Vrba et al. | 600/585 |

* cited by examiner

*Primary Examiner*—Todd E Manahan
*Assistant Examiner*—Michael G Mendoza
(74) *Attorney, Agent, or Firm*—Altera Law Group, LLC

(57) ABSTRACT

A guide wire for assisting in implantation and balancing of an orbital atherectomy device is disclosed. The guide wire is generally configured to be received within a driveshaft and cutting region of the orbital atherectomy device. The guide wire is sufficiently flexible to minimize trauma to the vessel walls when positioned within a patient. The distal end of the guide wire can include on or more weighted elements movable along the distal region of the guide wire to permit the balancing of an a rotating drive shaft and cutting region of an orbital atherectomy device. The guide wire can also include an atraumatic tip located on the end of the guide wire to reduce trauma to the vessels during implantation. Lubricious coatings are also provided to reduce friction between the driveshaft and cutting region of the atherectomy device and guide wire.

22 Claims, 6 Drawing Sheets

ORBITAL ATHERECTOMY DEVICE GUIDE WIRE DESIGN

This is a continuation-in-part of U.S. patent application filed Jan. 7, 2004 now abandoned, Ser. No. 10/753,040, and titled TERMINAL GUIDE FOR ROTATIONAL ATHERECTOMY DEVICE AND METHOD OF USING SAME.

BACKGROUND OF THE INVENTION

The present invention relates to medical devices and, more particularly, to guide wires for positioning and stabilization of intravascular medical devices.

Atherectomy devices are generally designed to remove stenotic occlusions from human arteries and bypass grafts. Atherectomy devices take a number of forms from mechanical cutting devices to various rotating abrading device.

The OAD consists of three stainless steel wires, helically wound to produce a device driveshaft. The OAD has an expanded, eccentric cross-section with an attached diamond surface "crown" located near the distal end. The OAD is revolved at rotational velocities up to 200,000 rpm, with the "crown's" abrasive surface removing stenotic tissue. The Orbital Atherectomy Device is deployed along and rotates around a pre-positioned guide wire.

A current guide wire design is shown in FIG. 1. As seen in the Figure, the guide wire G incorporates a flexible distal tip T that facilitates deployment of the guide wire G through the vascular system. The flexible tip T consists of polytetrafluoroethylene (PTFE) which is commercially available under the name Teflon® from E.I. du Pont de Nemours and Company. The flexible tip T is in the form of heat shrink tubing and is attached to the distal end D of the guide wire G. A flexible, distal, tubular portion P of the tip T can contain embedded platinum marker bands B at specified intervals to enhance radio-opacity. The flexible tip T with marker bands may extend approximately 25-30 mm past the distal end D of the guide wire G. The flexible tip permits the distal end of the guide wire G to be guided in a relatively atraumatic fashion to a desired location within the vasculature of a patient.

The following problems have been observed during deployment of the OAD over the pre-positioned guide wire:

With some prior guide wires, the distal end of the OAD may be extended over the PTFE tubing attached to the distal end of the guide wire shaft.

Further, the contact of the OAD driveshaft with the flexible PTFE tubing has been found to cause torsion and bending failure of the PTFE tubing with the failed segment difficult to extract.

In addition, the rotating OAD driveshaft inner surface creates surface erosion of the PTFE tubing, failing the PTFE tip, friction welding of the OAD to the guide wire, and resulting in premature failure of the OAD and/or the guide wire.

There is a need for an improved OAD guide wire design that addresses the above problems.

SUMMARY OF THE INVENTION

A guide wire for assisting in implantation and balancing of an orbital atherectomy device is disclosed. The guide wire is generally configured to be received within a driveshaft and cutting region of the orbital atherectomy device. The guide wire is sufficiently flexible to minimize trauma to the vessel walls is positioned within a patient. The distal end of the guide wire can include on or more weighted elements movable along the distal region of the guide wire to permit the balancing of an a rotating drive shaft and cutting region of an orbital atherectomy device. The guide wire can also include an atraumatic tip located on the end of the guide wire to reduce trauma to the vessels during implantation. Lubricious coatings are also provided to reduce friction between the driveshaft and cutting region of the atherectomy device and guide wire.

DETAILED DESCRIPTION OF THE PREFERRED EMBODIMENT

The present invention relates to a novel design for a guide wire that is generally illustrated throughout the figures as guide wire 10. The figures illustrate the guide wire 10 in particular embodiments and, in some figures, in conjunction with particular medical devices for ease of description and understanding. The figures are not intended to limit the possible applications of the present invention. The scope of the invention will be defined by the claims and will be understood by those skilled in the art upon review of the specification and figures.

Figure 1:
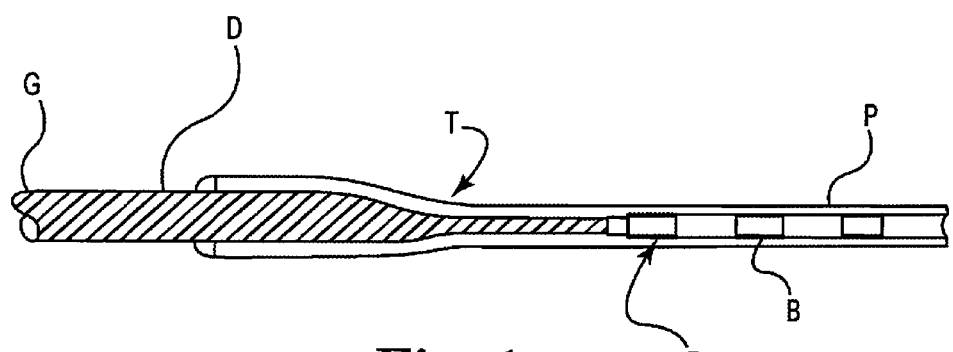
FIG. 1 illustrates an embodiment of a guide wire of the prior art.
Figure 2:
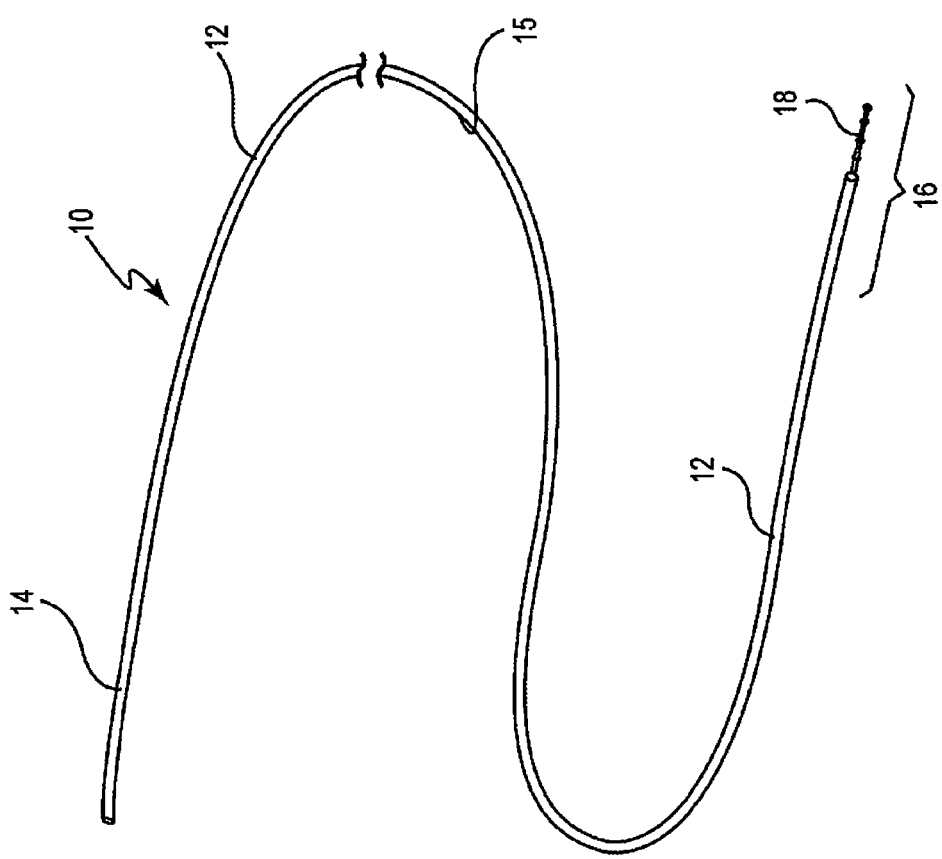
FIG. 2 illustrates a perspective view of an embodiment of a guide wire in accordance with the present invention.

Turning to FIG. 2, guide wire 10 is generally configured to permit distal region 16 of guide wire 10 to be positioned, relatively atraumatically, at a desired location within a patient. Accordingly, guide wire 10 is flexible and includes an atraumatic tip 18 to prevent damage to tissues as the guide wire is advanced.

Figure 3:
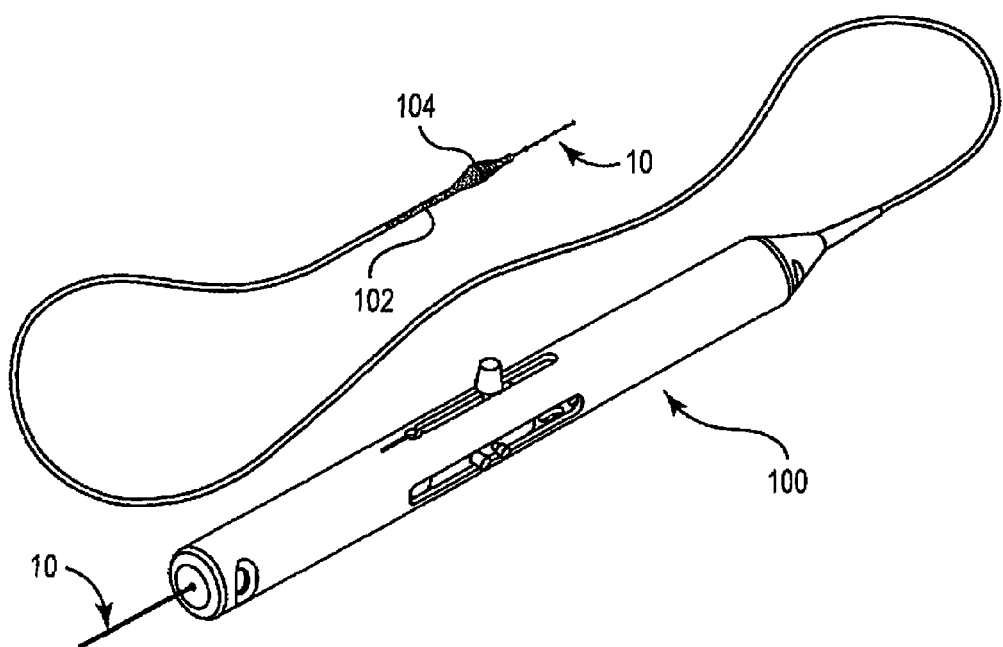
FIG. 3 illustrates a perspective view of an orbital atherectomy device using a guide wire in accordance with the present invention.

Guide wire 10 generally includes an elongated shaft 12 having a proximal region 14, a central region 15, and a distal region 16. Typically, elongated shaft 12 will have a circular cross-sectional shape although particular applications of the present invention may utilize alternative cross-sectional shapes in one or more regions of the guide wire. The shape, configuration and materials used to construct the shaft will determine the physical characteristics such as steerability and torquability and can vary with the particular end use for the guide wire 10. Similarly, guide wire 10 may be configured in a wide range of lengths and diameters depending on its application. For example, the guide wire can be between 180 to 325 centimeters in length and shaft 12 may have an outside diameter of about 0.009 inch for use in conjunction with a rotational atherectomy device 100, as shown in FIG. 3. To reduce the likelihood of adverse biological reactions, guide wire 10 is typically formed from biocompatible materials. These materials are commonly biocompatible metals or polymers.

Figure 4:
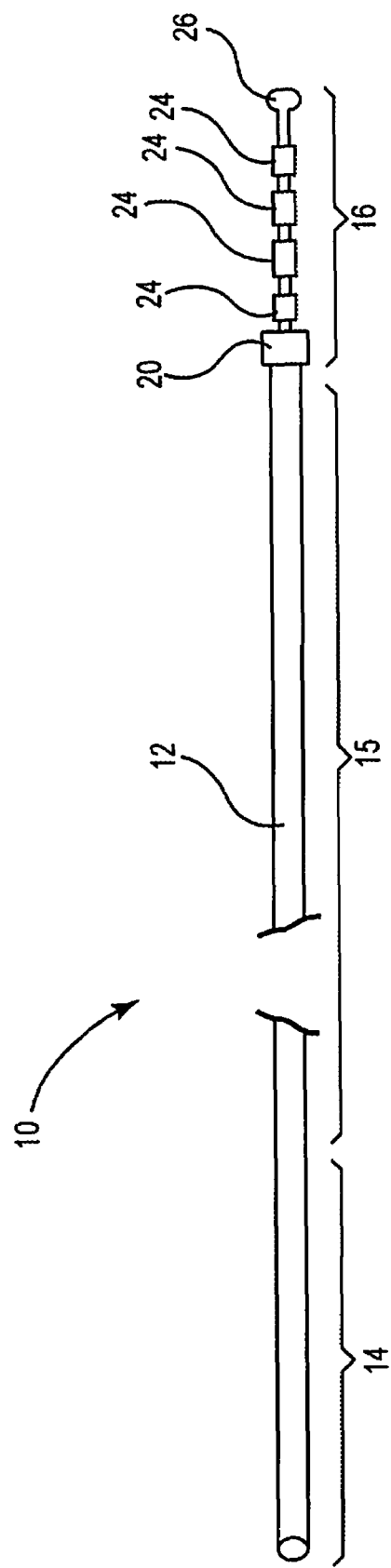
FIG. 4 illustrates an elevational view of an embodiment of a guide wire in accordance with the present invention.

In one aspect of the present invention (FIG. 4), the distal region 16 is provided with a proximal stop 20, one or more distal bodies 24 and a distal stop 26. The proximal stop 20 is generally configured as a region along the shaft 12 having an outside diameter greater than an adjacent region of the elongated shaft. The proximal stop 20 and the distal stop 26 are secured a desired distance apart from one another on the elongated shaft. Each distal body 24 is preferably slidably secured between the proximal stop 22 and the distal stop 26 about the elongated shaft 12 to permit the movement of the distal bodies along the longitudinal axis of the elongated shaft. Proximal stop 20 prevents the distal bodies 24 from sliding proximally beyond the proximal stop 20. Distal stop 26 prevents the distal bodies 24 from sliding distally beyond the distal stop 26. The region of elongated shaft 12 between the proximal stop 20 and distal stop 26 may have a reduced diameter relative to the proximal region and central region of shaft 12. The distal bodies 24 may be formed from a high density material giving the distal bodies a relatively high mass given their size. Whether formed from a high density material or otherwise, the movement of the distal bodies 24 between proximal stop 20 and distal stop 26 may function to alter the natural frequency response of the distal region of guide wire 10.

Figure 5:
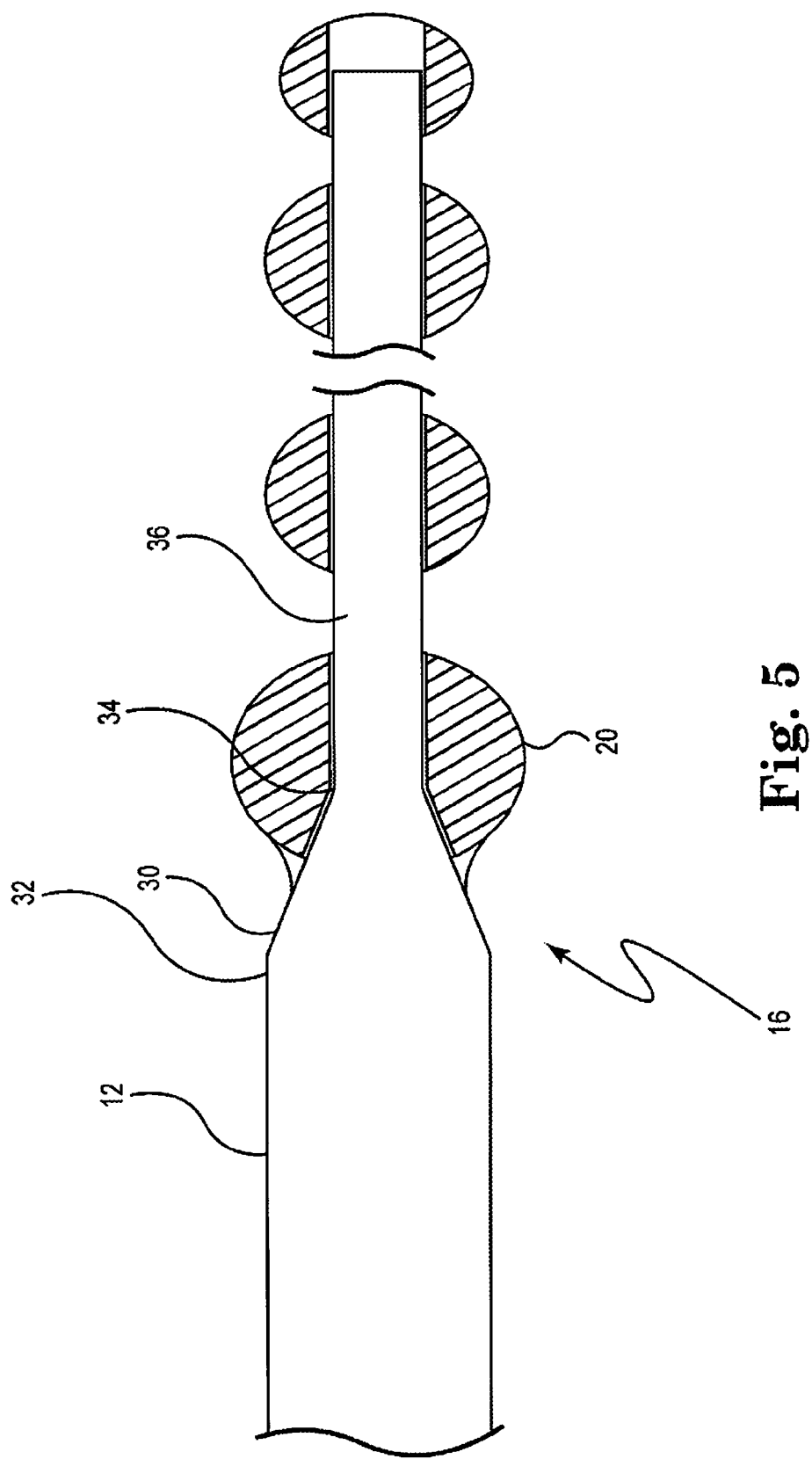
FIG. 5 illustrates a detailed elevational view of an embodiment of a guide wire in accordance with the present invention.

Turning to FIG. 5, the distal region 16 of the elongated shaft 12 may preferably include a gradually tapered region 30 transitioning from the maximum outer diameter of the guide wire shaft 32 to a specified reduced guide wire flexible tip outer diameter 34, then a specified portion 36 of constant outside diameter.

Proximal stop 20 is generally configured to prevent the proximal movement of the distal bodies 24. Proximal stop 20 may be an independent element secured to the elongated shaft 12 or may be an element integrally formed on the elongated shaft. The proximal stop 20 may generally be configured to reduce trauma during insertion of the guide wire 10 into a patient. The proximal stop 20 may take any number of forms which may prevent the proximal movement of distal bodies 24. The precise form which proximal stop 20 will take may vary with the configuration of the distal bodies 24. As illustrated for exemplary purposes, the proximal stop 20 extends circumferentially around the elongated shaft 12. In another configuration, proximal stop 20 may be formed by the transition from the diameter 32 of the elongated shaft 12 to a reduced diameter distal tip portion 34 of the shaft. As illustrated, proximal stop 20 is an independent element which defines a lumen through which elongated shaft 12 is positioned. The proximal stop 20 is preferably secured to the shaft by brazing.

Figure 6:
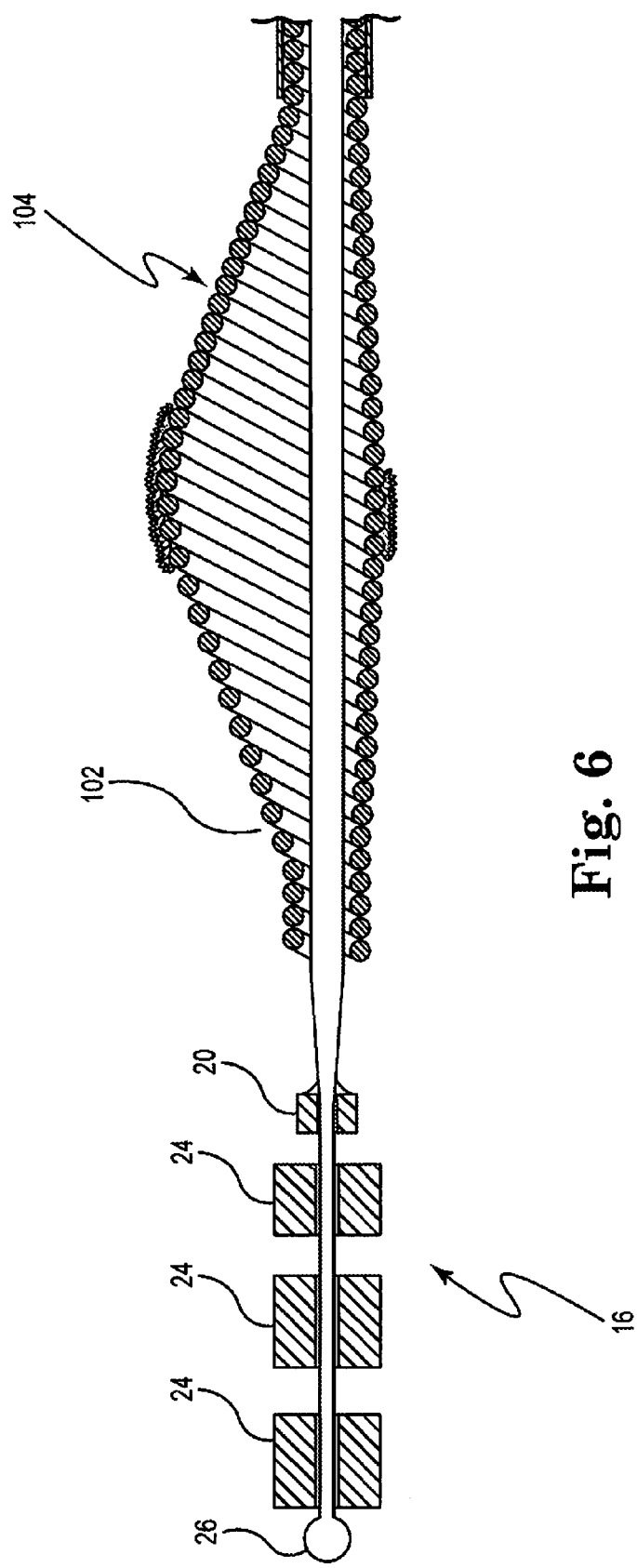
FIG. 6 illustrates an embodiment of an atherectomy device including an embodiment of a guide wire in accordance with the present invention.

The proximal stop 20 may also be configured to extend beyond the diameter 32 of the elongated shaft 12. In this configuration, the proximal stop 20 may extend from the elongated shaft a sufficient distance to prevent a drive shaft 102 of an atherectomy device 100, shown in FIG. 6, from advancing distally beyond the proximal stop 20.

When distal bodies 24 are configured to alter the frequency response of distal region 16 of guide wire 10, the present invention may provide a variable dynamic mass balancing system (VDMBS) which dampens the oscillation amplitudes of guide wire 10 when guide wire 10 is being used with a rotating atherectomy device or other type of guide wire positioned rotating medical device. In essence, this embodiment may provide a lumped mass system alone or a lumped mass system which varies the location of the center of mass in the distal region 16 of guide wire 10. The added mass of distal bodies 24 can alone alter the natural frequency of the distal region 16 of guide wire 10 sufficiently to prevent a resonance frequency condition from occurring during the operation of a rotating medical device. Alternatively, the movement of distal bodies 24 from the vibrations from a rotating medical device may alter the natural frequency of the distal region 16 of guide wire 10 sufficiently to prevent a resonance frequency condition from occurring during the operation of a rotating medical device.

In theory, the VDMBS may sufficiently separate the natural frequency response of the distal end 16 of guide wire 10 from the forcing force frequency of the rotating medical device such that a resonance frequency condition is not achievable. In another theory, the VDMBS may sufficiently separate the natural frequency response of the distal end 16 of guide wire 10 from the forcing force frequency of the rotating medical device such that the amplitude of the resultant distal region frequency response is less than the natural frequency response of the distal region without a lumped mass system alone or a lumped mass system with a variable center of mass location.

Furthermore, proximal stop 20, one or more distal bodies 24 and distal stop 26 may prevent the distal region from flexing beyond its breaking point during implantation. The flex limiting effect can be particularly advantageous when the distal region includes a reduced diameter section to increase flexibility. This advantage may be achieved by sizing and/or spacing the distal bodies such that one or more distal bodies 24 will come into contact with one another as distal region 16 is flexed to prevent substantial additional flexing of distal region 16 of shaft 12. In essence, distal bodies 24 may contact one another to prevent overflexing of shaft 12.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A guide wire, comprising:
   an elongated flexible shaft having a proximal region and a flexible distal region;
   a proximal stop secured to the flexible distal region of the elongated flexible shaft;
   a distal stop secured to the flexible distal region of the elongated flexible shaft; and
   at least one distal body, the at least one distal body being secured to the elongated flexible shaft between the proximal stop and the distal stop, wherein the at least one distal body has a center of mass with fixed location in the flexible distal region of the elongated flexible shaft between the proximal stop and the distal stop, and wherein the at least one distal body provides an oscillation amplitude balancing system having a center of mass which alters the natural frequency of the distal region of the guide wire sufficiently to prevent a resonance frequency condition from occurring during rotating operation, and wherein the at least one distal body comes into contact with another distal body as the distal region flexes.

2. The guide wire of claim 1, wherein the flexible distal region further comprises a tapered region.

3. The guide wire of claim 2, wherein the elongated flexible shaft has an outside diameter and the tapered region tapers from the outside diameter to a reduced outside diameter.

4. The guide wire of claim 3, wherein the proximal stop is present at the tapered region where the tapered region tapers from the outside diameter to the reduced outside diameter.

5. The guide wire of claim 4, wherein the proximal stop is a separate element that is secured to the tapered region.

6. The guide wire of claim 4, wherein the proximal stop is formed from the tapered region.

7. The guide wire of claim 1, wherein the outside diameter of the proximal stop is greater than the outside diameter of the elongated flexible shaft.

8. A flexible tip for a guide wire for positioning and stabilizing medical devices, the guide wire having an elongated flexible shaft with a proximal region and a flexible distal region, the flexible tip comprising:
   a proximal stop secured to the flexible distal region;
   a distal stop secured to the flexible distal region; and
   at least one distal body the at least one distal body being secured to the elongated flexible shaft between the proximal stop and the distal stop and having a center of mass located in the flexible distal region of the elongated flexible shaft between the proximal stop and the distal stop, wherein the at least one distal body dampens the oscillation amplitude of the guide wire, and wherein the at least one distal body comes into contact with another distal body as the distal region flexes thereby preventing overflexing of the flexible distal region.

9. The flexible tip of claim 8, wherein the at least one distal body is slidably engaged to the elongated flexible shaft and wherein the center of mass of the at least one distal body has a varying location between the proximal stop and the distal stop.

10. The flexible tip of claim 8, wherein the flexible distal region further comprises a tapered region.

11. The flexible tip of claim 10, wherein the elongated flexible shaft has an outside diameter and the tapered region tapers from the outside diameter to a reduced outside diameter.

12. The flexible tip of claim 11, wherein the proximal stop is present at the tapered region where the tapered region tapers from the outside diameter to the reduced outside diameter.

13. The flexible tip of claim 12, wherein the proximal stop is a separate element that is secured to the tapered region.

14. The flexible tip of claim 12, wherein the proximal stop is formed from the tapered region.

15. The flexible tip of claim 8, wherein the outside diameter of the proximal stop is greater than the outside diameter of the elongated flexible shaft.

16. A guide wire, comprising:
   an elongated flexible shaft having a proximal region and a flexible distal region;
   a proximal stop secured to the flexible distal region of the elongated flexible shaft;
   a distal stop secured to the flexible distal region of the elongated flexible shaft; and
   at least one distal body, the at least one distal body being slidingly secured to the elongated flexible shaft between the proximal stop and the distal stop, wherein the one distal body has a center of mass with varying location in the flexible distal region of the elongated flexible shaft between the proximal stop and the distal stop, and wherein the at least one distal body provides a variable dynamic oscillation amplitude balancing system which alters the natural frequency of the distal region of the guide wire sufficiently to prevent a resonance frequency condition from occurring during rotating operation, and wherein the at least one distal body comes into contact with another distal body as the distal region flexes.

17. The guide wire of claim 16, wherein the flexibledistal region further comprises a tapered region.

18. The guide wire of claim 17, wherein the elongated flexible shaft has an outside diameter and the tapered region tapers from the outside diameter to a reduced outside diameter.

19. The guide wire of claim 18, wherein the proximal stop is present at the tapered region where the tapered region tapers from the outside diameter to the reduced outside diameter.

20. The guide wire of claim 18, wherein the proximal stop is a separate element that is secured to the tapered region.

21. The guide wire of claim 17, wherein the proximal stop is formed from the tapered region.

22. The guide wire of claim 16, wherein the outside diameter of the proximal stop is greater than the outside diameter of the elongated flexible shaft.

* * * * *